(12) United States Patent
Kushla et al.

(10) Patent No.: US 6,599,531 B2
(45) Date of Patent: *Jul. 29, 2003

(54) METHOD OF MAKING IBUPROFEN AND NARCOTIC ANALGESIC COMPOSITIONS

(75) Inventors: Gregory P. Kushla, Florham Park, NJ (US); Jin-Wang Lai, Edison, NJ (US); Gerald P. Polli, Valley Forge, PA (US)

(73) Assignee: Knoll Pharmaceutical Company, Mt. Olive, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/028,939

(22) Filed: Dec. 21, 2001

(65) Prior Publication Data

US 2002/0127274 A1 Sep. 12, 2002

Related U.S. Application Data

(63) Continuation of application No. 08/872,217, filed on Jun. 10, 1997, now Pat. No. 6,361,794.
(60) Provisional application No. 60/020,973, filed on Jun. 12, 1996.

(51) Int. Cl.[7] .................................................. A61K 9/20
(52) U.S. Cl. ...................... 424/465; 424/464; 424/470; 424/493; 424/494; 424/468; 424/467
(58) Field of Search ................................. 424/465, 464, 424/470, 493, 494, 468, 469, 489

(56) References Cited

U.S. PATENT DOCUMENTS

| | | | |
|---|---|---|---|
| 3,385,886 A | 5/1968 | Nicholson et al. | 260/515 |
| 3,393,197 A | 7/1968 | Pachter et al. | 260/285 |
| 3,755,427 A | 8/1973 | Adams et al. | 260/515 A |
| 3,792,170 A | 2/1974 | Shen et al. | 424/303 |
| 3,865,949 A | 2/1975 | Greig | 424/317 |
| 3,936,528 A | 2/1976 | Katz | 424/260 |
| 4,083,981 A | 4/1978 | Yamamoto et al. | 424/260 |
| 4,132,788 A | 1/1979 | Wong | 424/232 |
| 4,156,002 A | 5/1979 | Brown et al. | 424/249 |
| 4,176,194 A | 11/1979 | Waring | 424/309 |
| 4,205,087 A | 5/1980 | Waring | 424/317 |
| 4,237,140 A | 12/1980 | Dudzinski | 424/260 |

(List continued on next page.)

FOREIGN PATENT DOCUMENTS

| | | |
|---|---|---|
| EP | 0 068 838 A1 | 1/1983 |
| WO | WO 91/17740 A1 | 11/1991 |
| WO | WO 91/17747 A1 | 11/1991 |
| WO | WO 92/05768 A1 | 4/1992 |
| WO | WO 92/05769 A1 | 4/1992 |

OTHER PUBLICATIONS

Graves, D.A., et al., "Extraordinary Analgesic Requirement in a Patient Previously Unexposed to Narcotics", *Drug Intelligence and Clinical Pharmacy* 18: 598–600 (Jul./Aug. 1984).

(List continued on next page.)

*Primary Examiner*—Gollamudi S. Kishore
*Assistant Examiner*—Robert M. Joynes
(74) *Attorney, Agent, or Firm*—Lahive & Cockfield, LLP; Peter C. Lauro, Esq.

(57) ABSTRACT

Provided herein are compositions and methods of making compositions of ibuprofen in combination with a narcotic analgesic. Specifically provided is a pharmaceutical tablet composition comprising ibuprofen; a narcotic analgesic; colloidal silicon dioxide; a filler selected from the group consisting of microcrystalline cellulose and powdered cellulose; a disintegrant selected from the group consisting of croscarmellose sodium, crospovidone, and sodium starch glycolate; a binder consisting of an akylhydroxy methylcellulose; a starch; and a lubricant. Also provided is a method of preparing a pharmaceutical tablet composition comprising: (a) Granulating ibuprofen, a narcotic analgesic, a first glidant, a first disintegrant, a binder, and starch to form granules wherein said granulating step comprises a wet granulation process; (b) blending the granules with extra-granular material comprised of a second glidant, a second disintegrant, a filler and starch to form a blend of granules and extra-granular material; and (c) compressing the blend into a tablet.

36 Claims, 2 Drawing Sheets

U.S. PATENT DOCUMENTS

| | | | |
|---|---|---|---|
| 4,254,122 A | 3/1981 | Brown | 424/249 |
| 4,282,215 A | 8/1981 | Dudzinski et al. | 424/232 |
| 4,308,251 A | 12/1981 | Dunn et al. | 424/19 |
| 4,361,580 A | 11/1982 | Peck et al. | 424/287 |
| 4,366,159 A | 12/1982 | Magruder | 424/260 |
| 4,379,789 A | 4/1983 | Capetola et al. | 424/260 |
| 4,402,962 A | 9/1983 | Schmidt | 424/260 |
| 4,404,208 A | 9/1983 | Schmidt | 424/260 |
| 4,404,209 A | 9/1983 | Schmidt | 424/260 |
| 4,404,210 A | 9/1983 | Schmidt | 424/260 |
| 4,404,211 A | 9/1983 | Schmidt | 424/260 |
| 4,407,804 A | 10/1983 | Schmidt | 424/260 |
| 4,407,805 A | 10/1983 | Schmidt | 424/260 |
| 4,420,483 A | 12/1983 | Sunshine et al. | 424/253 |
| 4,439,453 A | 3/1984 | Vogel | 424/324 |
| 4,443,476 A | 4/1984 | Lomen | 424/317 |
| 4,464,376 A | 8/1984 | Sunshine et al. | 424/253 |
| 4,466,963 A | 8/1984 | Cavalla et al. | 424/244 |
| 4,479,956 A | 10/1984 | Sunshine et al. | 424/253 |
| 4,486,436 A | 12/1984 | Sunshine et al. | 424/253 |
| 4,489,080 A | 12/1984 | Lomen | 424/260 |
| 4,522,826 A | 6/1985 | Sunshine et al. | 514/569 |
| 4,552,899 A | 11/1985 | Sunshine et al. | 514/568 |
| 4,558,051 A | 12/1985 | Sunshine et al. | 514/261 |
| 4,569,937 A | 2/1986 | Baker et al. | 514/282 |
| 4,571,400 A | 2/1986 | Arnold | 514/282 |
| 4,587,249 A | 5/1986 | Sunshine et al. | 514/265 |
| 4,587,252 A | 5/1986 | Arnold | 514/282 |
| 4,609,675 A | 9/1986 | Franz | 514/568 |
| 4,690,927 A | 9/1987 | Voss et al. | 514/282 |
| 4,783,465 A | 11/1988 | Sunshine et al. | 514/255 |
| 4,806,359 A | 2/1989 | Radebaugh et al. | 424/470 |
| 4,829,064 A | 5/1989 | Sunshine et al. | 514/255 |
| 4,837,031 A | 6/1989 | Denton | 424/464 |
| 4,839,176 A | 6/1989 | Pankhania et al. | 424/465 |
| 4,844,907 A | 7/1989 | Elger et al. | 424/465 |
| 4,851,444 A | 7/1989 | Sunshine et al. | 514/570 |
| 4,859,704 A | 8/1989 | Haas | 514/551 |
| 4,868,214 A | 9/1989 | Sunshine et al. | 514/568 |
| 4,882,167 A | 11/1989 | Jang | 424/468 |
| 4,883,818 A | 11/1989 | Sunshine et al. | 514/570 |
| 4,904,477 A | 2/1990 | Ho et al. | 424/465 |
| 4,911,921 A | 3/1990 | Denton et al. | 514/570 |
| 4,920,149 A | 4/1990 | Sunshine et al. | 514/557 |
| 4,927,854 A | 5/1990 | Sunshine et al. | 514/570 |
| 4,962,124 A | 10/1990 | Sunshine et al. | 514/568 |
| 4,980,375 A | 12/1990 | Sunshine et al. | 514/570 |
| 5,087,454 A | 2/1992 | Duerholz et al. | 424/464 |
| 5,100,918 A | 3/1992 | Sunshine et al. | 514/557 |
| 5,164,398 A | 11/1992 | Sims et al. | 514/282 |
| 5,191,114 A | 3/1993 | Chen | 562/496 |
| 5,200,193 A | 4/1993 | Radebaugh et al. | 424/468 |
| 5,256,699 A | 10/1993 | Murphy et al. | 514/658 |
| 5,395,627 A | 3/1995 | Dopper et al. | 424/489 |
| 5,424,075 A | 6/1995 | Daher et al. | 424/465 |
| 5,462,747 A | 10/1995 | Radebaugh et al. | 424/465 |
| 5,464,633 A | 11/1995 | Conte et al. | 424/480 |
| 5,565,613 A | 10/1996 | Geisslinger et al. | 562/496 |
| 5,681,577 A | 10/1997 | Lech et al. | 424/439 |
| 5,681,583 A | 10/1997 | Conte et al. | 424/472 |
| 5,686,107 A | 11/1997 | Ratnaraj et al. | 424/464 |
| 5,686,109 A | 11/1997 | Fujitsu et al. | 424/464 |
| 5,869,102 A | 2/1999 | Stroppolo et al. | 424/465 |
| 6,348,216 B1 * | 2/2002 | Kushla et al. | 424/465 |
| 6,361,794 B1 * | 3/2002 | Kushla et al. | 424/465 |

OTHER PUBLICATIONS

Ferrer–Brechner, T., et al., "Combination Therapy with Ibuprofen and Methadone for Chronic Cancer Pain", *The American Journal of Medicine*, 78–83 (Jul. 13, 1984).

McGivney, W.T., et al., "The Care of Patients with Severe Chronic Pain in Terminal Illness", *Journal of American Medical Association* 251(9): 1182–1188 (Mar. 2, 1984).

Cooper, S.A. et al., "Analgesic Efficacy of an Ibuprofen–Codeine Combination", *Pharmacotherapy* 2(3): 162–167 (May/Jun. 1982).

Cooper, S.A. et al., "Relative Efficacy of An Ibuprofen–Codeine Combination", *Clin. Pharmacol. Ther.*. 27(2): 249 (Feb. 1980).

Beaver, W.T., et al., "Methodological Considerations in the Evaluation of Analgesic Combinations: Acetaminophen (Paracetamol) and Hydrocodone in Postpartum Pain", *Br. J. Clin. Pharmac.* 10: 215S–223S (1980).

Lachman, L. "The Theory and Practice of Industrial Pharmacy" 325–336 (1929, Great Britain).

Motrin, *Physician's Desk Reference* (PDR), pp. 2435–2436 (48th Ed., Medial Economics Data Production Company, Montvale, (NJ) (1994).

Ibuprofen, *Physician's Desk Reference*, pp. 626–628 (48th Ed., Medial Economics Data Production Company, Montvale, NJ) (1994).

Ibuprofen, *Physician's Desk Reference*, 1389–91 (51st Ed., Medial Economics Company, Montvale, NJ) (1997).

Memorandum opinion and order, Knoll Pharmaceutical Co., Inc. amd John and Lois Arnold Family Ltd., LLP v. Teva Pharmaceuticals USA, Inc., In the US District Court for the Northern District of Illinois Eastern Division, Case No. 01C1646.

PCT/US97/09819 ISR Sep. 29, 1997.

Beaver, W.T., "Aspirin and Acetaminophen as Constituents of Analgesic Combinations", *Arch. Intern. Med.* 141: 293–300 (Feb. 23, 1981).

U.S. patent application Ser. No. 10/027,248, filed Dec. 2001.

* cited by examiner

METHOD OF MAKING IBUPROFEN AND NARCOTIC ANALGESIC COMPOSITIONS This application is a continuation of U.S. application Ser. No. 08/872,217, entitled "Method of Making Ibuprofen and Narcotic Analgesic Compositions", filed on Jun. 10, 1997, now U.S. Pat. No. 6,361,794 which claims priority to U.S. Provisional Patent Application Serial No. 60/020,973, filed Jun. 12, 1996. The contents of the aforementioned applications are hereby incorporated herein by reference.

FIELD OF THE INVENTION

This invention is related to the field of pharmaceutical compositions and methods of preparing pharmaceutical compositions. Specifically, this invention is related to solid dosage compositions of ibuprofen in combination with a narcotic analgesic.

BACKGROUND OF THE INVENTION

Solid dosage forms of ibuprofen, a non-steroidal anti-inflammatory agent, are known. Although tablet compositions of ibuprofen are known and commercially available, problems of poor tablet compression, stability and disintegration persist and are well documented. For example, it is known that ibuprofen tablets made from wet granulation methods "age" over time which tends to have a negative impact on dissolution. (See U.S. Pat. No. 4,609,675 to Franz). Franz theorizes that the tablets "age" over time because of sintering which is described as a type of cementing of the ibuprofen particles to one another. Franz states that one way to minimize sintering is to increase the amount of excipients or diluents used in the compositions in order to isolate the ibuprofen particles. This causes problems in formulating high dose ibuprofen tablets because the tablets are too large when they are made by a wet granulation process. In an effort to overcome this problem, Franz prepared a dry granulation of high dose ibuprofen in combination with croscarmellose, noting that it was unexpected to formulate a successful composition in view of his experience that other disintegrants such as corn starch and crospovidone did not work. Franz also describes that croscarmellose improved dissolution characteristics of the tablets when they contained 1.34% to 7.01% croscarmellose but decreased dissolution characteristics when the tablets contained croscarmellose in excess of 7.01%.

U.S. Pat. No. 4,911,921 to Denton et al. notes that they were able to overcome the problem of using a large amount of excipients in wet granulation methods used to make ibuprofen tablets. Denton et al. notes that Franz was able to overcome these problems by using a dry mixing method using amounts of croscarmellose up to 15% and preferably about 7 to 8%. Denton describes the use of agglomerates of ibuprofen and binder held together by binder and polyvinylpyrrolidone. Denton et al. describes the use of a dry composition comprised of lactose.

Solid dosage forms of non-steroidal anti-inflammatory agents in combination with narcotic analgesics are known and have been described as providing a synergistic therapeutic for the relief of pain. For example, U.S. Pat. No. 4,690,927 to Voss et al describes the preparation of diclofenac sodium and codeine phosphate tablets by mixing the diclofenac sodium and codeine with dicalcium phosphate, corn starch and colloidal silica. In Voss et al. the mixture is spray granulated with a solution of hydroxypropyl cellulose in dioinized water. The dried granulation is mixed with carboxymethyl starch, colloidal silica and magnesium stearate. The resulting blend is compressed into tablets and film coated.

U.S. Pat. No. 4,587,252 to Arnold describes the treatment of pain using a combination of ibuprofen and hydrocodone. Arnold describes tablets containing flavoring agents, lubricants, solubilisers, suspending agents, binders, and disintegrants. Although Arnold lists many different ingredients that can be used in the tablets, the examples are directed to tablets that contain, along with other compounds, hydrocodone bitartrate, ibuprofen, microcrystalline cellulose, and magnesium stearate. The method of making the tablets is directed to a dry granulation process.

European Patent Application No. 68838A (Upjohn) also describes a combination product of a narcotic analgesic and ibuprofen. The tablets are generally described as containing agents such as diluents, binders, gelating solutions and methylcellulose. Specifically described tablets are directed to tablets containing lactose, corn starch, magnesium stearate and light liquid petrolatum.

Although solid dosage forms of non-steroidal anti-inflammatory agents in combination with narcotic analgesics are known, workers have discussed problems with formulating tablets containing both an analgesic narcotic and a non-steroidal anti-inflammatory drug. U.S. Pat. No. 4,839,176 to Pankhania et al. describes a wet granulation method for making various strength ibuprofen and codeine phosphate tablets. The ibuprofen is mixed with microcrystalline cellulose, calcium carboxymethylcellulose and fumed silica. This combination of material is granulated using a solution of polyvinylpyrrolidone in isopropyl alcohol. The granules are sized, dried and blended with excipients such as calcium carboxymethylcellulose, fumed silica, stearic acid, and sodium metabilsulphite. Pankhania et al. states that the formulations are unexpectedly stable over time in view of the general knowledge that admixtures of ibuprofen and codeine are unsatisfactory for commercial use.

U.S. Pat. No. 4,844,907 to Elger describes multiphase tablets prepared by compressing narcotic analgesic granules with non-steroidal anti-inflammatory granules. Both granules are described as being prepared in the absence of magnesium stearate. Elger states that tablets made with a narcotic analgesic, a non-steroidal anti-inflammatory carboxylic acid and magnesium stearate, as described in European Patent Application Number 68838A, exhibit serious incompatibility, poor crushing strength and long disintegration times. Elger also presents comparative examples of "single phase" tablets with ibuprofen, codeine, microcrystalline cellulose and croscarmellose sodium and states that these tablets had poor disintegration times, poor crushing strengths or sticking problems.

The above discussion indicates that compositions made from both wet and dry granulation processes have not been completely effective in providing a composition with both ibuprofen and a narcotic analgesic wherein the composition has acceptable disintegration, dissolution and compression characteristics. The inventors have also found that direct compression methods produce compositions with poor content uniformity. The inventors have further found that direct compression methods produce tablets that have poor compressibility.

Thus, it is an object of the present invention to provide a composition containing ibuprofen and a narcotic analgesic having superior disintegration, dissolution and compression characteristics.

SUMMARY OF THE INVENTION

Figure 1:
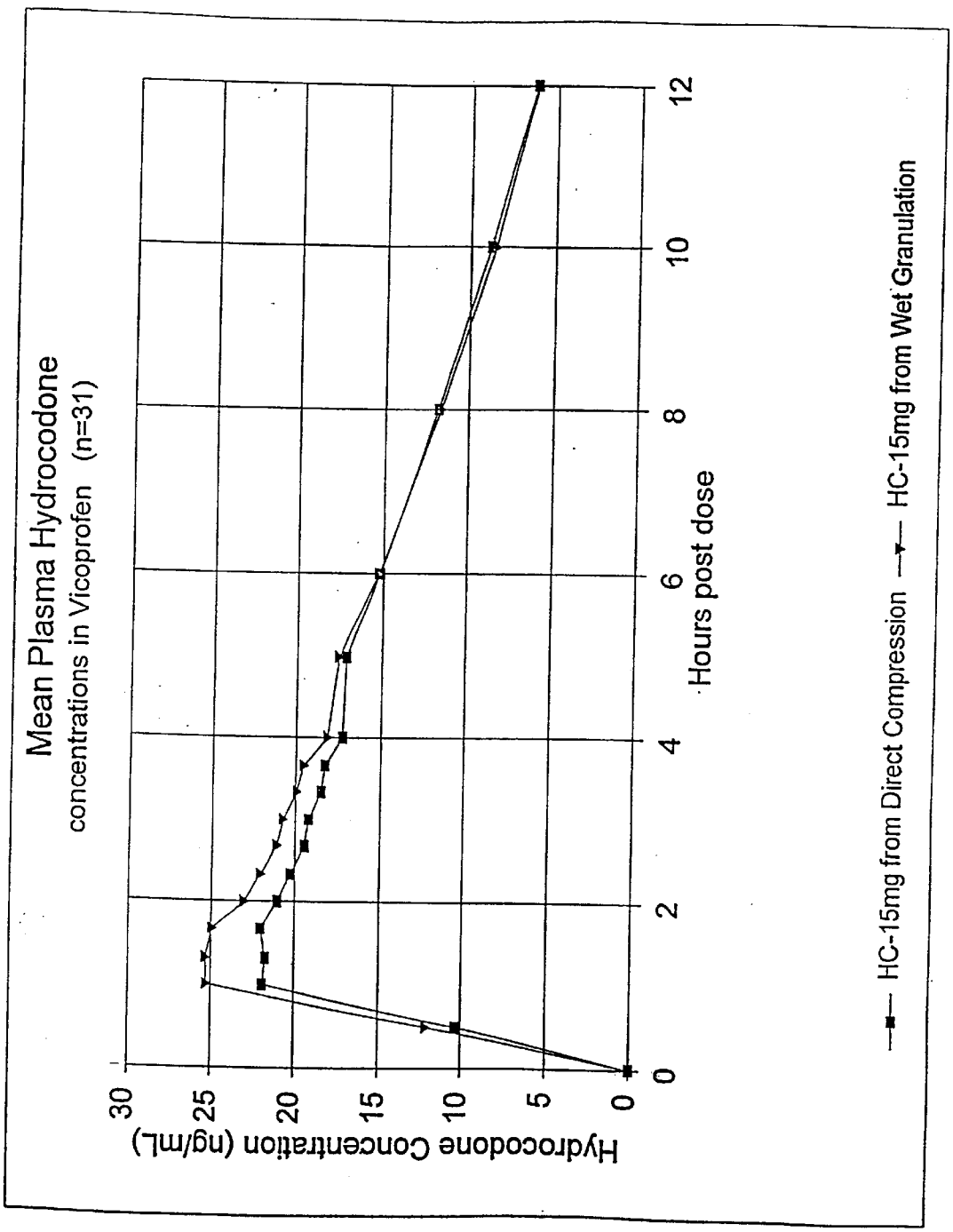
FIG. 1 is a graph of the plasma concentration of hydrocodone over time provided by an embodiment of the present invention.

Provided herein is pharmaceutical composition comprising a granule comprised of ibuprofen and a narcotic analgesic in a single phase. The composition may also comprise a blend of the granule and extra granule material. Preferably, the blend is compressed into a table composition.

In another aspect of the present invention a tablet composition is provided containing an effective amount of ibuprofen; an effective amount of a narcotic analgesic; colloidal silicon dioxide; a filler; a disintegrant; a binder; a starch; and a lubricant. The tablet is made by compressing a blend of a granule and extra granule material wherein the granule comprises at least a portion of the ibuprofen, at least a portion of the narcotic analgesic, a portion of the colloidal silicon dioxide, a portion of the disintegrant, a portion of the filler and a portion of the starch. The weight of the extra granule material is provided in a range of up to about 25% of the weight of the whole tablet. Surprisingly, an effective amount of a narcotic analgesic may be included with the ibuprofen in the granule in a single phase.

Also provided herein is a method of preparing a pharmaceutical tablet composition comprising:

(a) Granulating ibuprofen, a narcotic analgesic, a first glidant, a first disintegrant, a binder, and starch to form granules wherein said granulating step comprises a wet granulation process;

(b) blending the granules with extra-granular material comprised of a second glidant, a second disintegrant, a filler and starch to form a blend of granules and extra-granular material; and (c) compressing the blend into a tablet.

The compositions of the invention are used in the treatment of pain or inflammation or both in a mammal, preferably a human patient, by administering Arid) to the mammal an effective amount of the compositions described herein.

DETAILED DESCRIPTION OF THE INVENTION

In practicing the invention it is preferred that the weight of the colloidal silicon dioxide is in a range, of the total weight of the tablet, of about 0.5% to about 3%, most preferably about 1.5% to about 2%. The weight of the alkylhydroxy methylcellulose is preferably provided in a range, of the total weight of the tablet composition, of about 2% to less than 6%, most preferably at about 3% to about 4%. The filler is selected from the group consisting of microcrystalline cellulose and powdered cellulose and is provided in a weight range, of the total weight of the tablet, of about 10% to about 42%, preferably from 15% to about 25%.

The disintegrant is selected from the group consisting of croscarmellose sodium, crospovidone, and sodium starch glycolate and the weight of the disintegrant is preferably provided in a range, of the total weight of the tablet composition, of about 4% to about 10%, most preferably about 6% to about 8%. The starch is preferably provided in a weight range, of the total weight of the tablet composition, of about 11% to about 20%, most preferably about 11 to about 17%. The lubricant is preferably provided in an amount less than about 1% by weight of the total weight of the tablet.

The amount of ibuprofen is provided in a weight range of about 25% to about 63%, most preferably at 50%. The preferred narcotic analgesic is hydrocodone and is provided in an effective amount, preferably about 0.6% to about 3.8%, most preferably at 1.88% of the total weight of the tablet.

In practicing embodiments of the herein described invention a granulate is formed by first blending a granulate material. The granulate material comprises ibuprofen, a narcotic analgesic, and at least one excipient. The excipient may comprise, separately or together, colloidal silicon dioxide, a first disintegrant, a binder and starch. The granulate material may comprise all of the ibuprofen and the narcotic analgesic. The weight of the colloidal silicon dioxide in the granule is about 0.5% to about 2.0%, most preferably at about 0.75% of the total weight of the tablet. The first disintegrant of the granulate is preferably croscarmellose provided in an weight of up to about 4.0% of the total weight of the tablet. The binder of the granulate is preferably an akylhydroxy methylcellulose provided in a weight of about 2% to less than 6%, most preferably at about 3.3% of the total weight of the tablet. The starch of the granulate is preferably corn starch and is preferably provided in a range of about 6% to about 12%, most preferably at about 12% of the total weight of the tablet. A first filler may also be provided in the granulate wherein the filler is selected from the group consisting of microcrystalline cellulose and powdered cellulose and is provided in the granulation in a weight range of about up to 22% of the total weight of the tablet.

In a preferred emobiedment of the herein described invention the granulate is formed by adding water or other wetting agents to the granulate material and mixing until moist agglomerates are formed. The agglomerates are dried until a dried granulate is formed. The granulate is milled until a find blend having a uniform particle size is obtained.

The granulate is mixed with the remaining extra granulate material comprised of colloidal silicon dioxide, a second distintegrant, a filler, and starch. The second distintegrant is preferably the same material as the first disintegrant. The filler may comprise a second filler and may be of the same material as the first MID filler. The weight of the extra granular material is preferably up to about 25% of the total weight of the tablet.

The resulting blend is compressed into tablets.

The most preferred formulation made by the above described method comprises:

(a) about 50% ibuprofen;

(b) about 1.88% hydrocodone bitartrate;

(c) about 1.5% colloidal silicon dioxide;

(d) about 19.3% microcrystalline cellulose;

(e) about 8% sodium croscarmellose;

(f) about 3.25% hydroxypropyl methylcellulose;

(g) about 15.6% corn starch; and (h) about 0.5% magnesium stearate wherein the total percent of the tablet material is equal to about 100% of the weight of the tablet; wherein the tablet comprises a compressed blend of a granule and extra granule material wherein the granule comprises, as a portion of the tablet material that comprises the total weight of the tablet:

(a) about 50% ibuprofen;
(b) about 1.9% hydrocodone bitartrate:
(c) about 0.75% colloidal silicon dioxide
(d) about 9.5% microcrystalline cellulose;
(e) about 4.0% croscarmellose sodium;
(f) about 10.6% corn starch; and
(g) about 3.3% hydroxypropyl methylcellulose;
and the extra granule material comprises the remaining tablet material.

The inventors found that they were able to formulate a pharmaceutical tablet from a wet granulation process wherein a non-steroidal anti-inflammatory agent is present in a single phase with a narcotic analgesic and a lubricant. Compositions and methods described herein are provided in the substantial absence of lactose and polyvinylpyrrolidone either alone or in combination.

Tablets of the present invention may be compressed across a wide area of compression forces such as from 5 to 20 kN with no substantial change in the disintegration time of the tablet. Embodiments of the present invention are stable up to about 12 month(s) at 25° C., 60% relative humidity. That is, there is no substantial change in dissolution characteristics or no substantial change in disintegration time after 12 months.

Preferred embodiments of the invention also showed no significant changes in dissolution characteristics or disintegration time when stored at 40° C., 75% relative humidity for up to 6 months. The stability of such compositions at accelerated conditions indicate that long term stability at room temperature can be expected.

The present invention also provides for superior dissolution. Preferably, not less than 70% of the ibuprofen or hydrocodone is released at 30 minutes in 900 ml 5 of pH phosphate buffer, at 37° C. using baskets at 150 revolutions per minute. In preferred compositions 100% of the ibuprofen and the hydrocodone is released in 10 minutes.

It was found that the compositions made according to the present invention flow well and have good compression performance since they can be compressed ID over a wide range of compression forces and are relatively insensitive to press speed.

Compositions made with hydrocodone and lactose were not physically stable and did not flow well. These compositions also had large weight variation and relatively long disintegration times.

In practicing the invention the above described tablets may be film coated and also contain colorants, sweeteners, and flavorants.

Examples are provided below and are illustrative only and are not meant to limit the invention in any manner.

EXAMPLE 1

Twenty-six (twenty unique and five original) samples were prepared comprising ibuprofen; colloidal silicon dioxide; croscarmellose sodium; corn starch; powdered cellulose; hydroxypropyl methylcellulose; and microcrystalline cellulose. The ingredients were formulated to make 400 mg tablets. The range of ingredients of the compositions are as listed in Table 1.

TABLE 1

| Ingredient | Quantity (mg) | Percent (wt.) |
|---|---|---|
| Ibuprofen | 200 | 50.0 |
| colloidal silicon dioxide | 3 | 0.75 |
| croscarmellose sodium | 16 | 4.00 |
| corn starch | 24–28 | 6.00–12.00 |
| powdered cellulose | 0–85 | 0–21.25 |
| hydroxypropyl methyl cellulose | 12–24 | 3.00–6.00 |
| colloidal silicon dioxide | 4 | 1.00 |
| croscarmellose sodium | 16 | 4.00 |
| microcrystalline cellulose | 40–80 | 10.00–20.00 |
| corn starch | 0–20 | 0–5.00 |
| Total | 400 | 100.00 |

Granulate material was formed by mixing the ibuprofen, colloidal silicon dioxide, croscarmellose, corn starch, powdered cellulose, and hydroxypropyl methylcellulose to form a blend. Water was added to the blend to form a wet mixture. The water was dried from the wet mixture and a granulate was formed. The granulate was then mixed with colloidal silicon dioxide, croscarmellose sodium, microcrystalline cellulose and corn starch. Tablets were formed using 5, 12.5 and 20 kN of compression.

The compositions that were prepared and their specific ingredients are displayed in Table 2.

TABLE 2

| Batch Code | Exp. Number | CSI | E | B | AV | CSE |
|---|---|---|---|---|---|---|
| A | 8 | 6.00 | 18.25 | 6.00 | 10.00 | 0 |
| B | 1 | 6.00 | 21.25 | 3.00 | 10.00 | 0 |
| C | 17 | 6.00 | 8.75 | 3.00 | 20.00 | 2.50 |
| D | 11 | 9.00 | 13.25 | 3.00 | 10.00 | 5.00 |
| E | 16 | 9.25 | 6.50 | 6.00 | 15.75 | 2.75 |
| F | 12 | 6.00 | 13.25 | 6.00 | 10.00 | 5.00 |
| G | 9 | 6.00 | 3.25 | 6.00 | 20.00 | 5.00 |
| H | 5 | 6.00 | 11.25 | 3.00 | 15.00 | 5.00 |
| I | 1 | 6.00 | 21.25 | 3.00 | 10.00 | 0 |
| J | 14 | 12.00 | 12.25 | 6.00 | 10.00 | 0 |
| K | 19 | 6.00 | 14.75 | 4.50 | 10.00 | 5.00 |
| L | 10 | 12.00 | 0 | 6.00 | 17.25 | 5.00 |
| M | 3 | 12.00 | 7.25 | 6.00 | 10.00 | 5.00 |
| N | 15 | 6.00 | 9.75 | 4.50 | 20.00 | 0 |
| O | 6 | 12.00 | 10.25 | 3.00 | 15.00 | 0 |
| P | 13 | 9.00 | 8.25 | 3.00 | 20.00 | 0 |
| Q | 3 | 12.00 | 7.25 | 6.00 | 10.00 | 5.00 |
| R | 4 | 6.00 | 8.25 | 6.00 | 20.00 | 0 |
| S | 5 | 6.00 | 11.25 | 3.00 | 15.00 | 5.00 |
| T | 20 | 9.00 | 14.25 | 4.50 | 10.00 | 2.50 |
| U | 2 | 12.00 | 0 | 3.25 | 20.00 | 5.00 |
| V | 18 | 12.00 | 12.75 | 3.00 | 10.00 | 2.50 |
| W | 7 | 12.00 | 2.25 | 6.00 | 20.00 | 0 |
| X | 2 | 12.00 | 0 | 3.25 | 20.00 | 5.00 |
| Y | 4 | 6.00 | 8.25 | 6.00 | 20.00 | 0 |

CSI = corn starch, intragranular
E = powdered cellulose (Elcema P-100)
B = binder (Methocel E15 LVP)
AV = microcrystalline cellulose (Avicel PH 102)
CSE = corn starch. extragranular Hardness, thickness, disintegration, friability, tablet weight, and tablet density were measured. The results are listed in Tables 3–5.

TABLE 3

In-process physical characteristics [mean (sd)] of ibuprofen tablets compressed at 5 kN

| Batch Code | Hardness (SCU) | Thickness (mm) | Disint. (s) | Friability (%) 6 min | Friability (%) 12 min | Weight Var. (%) | Tablet Density (g/mL) |
|---|---|---|---|---|---|---|---|
| A | 8.2 (1.0) | 5.87 (0.01) | 57 (3) | 0.06 | 0.20 | 2.68 | 0.99 |
| B | 12.3 (0.9) | 5.73 (0.01) | 44 (8) | 0.07 | 0.15 | 0.88 | 1.06 |
| C | 12.6 (0.9) | 5.56 (0.01) | 145 (30) | 0.16 | 0.17 | 1.05 | 1.08 |
| D | 10.7 (1.2) | 5.62 (0.01) | 165 (8) | 0.07 | 0.23 | 1.20 | 1.07 |
| E | 11.2 (1.3) | 7.70 (0.01) | 197 (46) | 0.07 | 0.12 | 1.72 | 1.06 |
| F | 12.3 (3.1) | 5.63 (0.02) | 208 (34) | 0.08 | 0.18 | 4.65 | 1 07 |
| G | 10.8 (1.0) | 5.56 (0.02) | 209 (30) | 0.10 | 0.28 | 1.28 | 1.06 |
| H | 14.3 (2.6) | 5.47 (0.02) | 162 (14) | 0.10 | 0.19 | 2.45 | 1.10 |
| I | 11.2 (0.7) | 5.63 (0.01) | 101 (21) | 0.05 | 0.09 | 1.29 | 1.05 |
| J | 11.1 (3.4) | 5.66 (0.03) | 191 (38) | 0.01 | 0.04 | 3.31 | 1.05 |
| K | 9.5 (0.7) | 5.62 (0.01) | 229 (15) | 0.01 | 0.03 | 1.93 | 1.04 |
| L | 10.2 (0.3) | 5.68 (0.01) | 429 (65) | 0.22 | 0.32 | 1.49 | 1.07 |
| M | 10.2 (0.7) | 5.71 (0.01) | 379 (48) | 0.18 | 0.29 | 0.95 | 1.06 |
| N | 12.0 (1.2) | 5.68 (0.02) | 110 (13) | 0.14 | 0.20 | 1.36 | 1.05 |
| O | 11.4 (0.9) | 5.69 (0.01) | 162 (12) | 0.11 | 0.25 | 0.68 | 1.06 |
| P | 13.3 (1.2) | 5.63 (0.02) | 137 (18) | 0.11 | 0.21 | 1.05 | 1.08 |
| Q | 8.5 (1.2) | 5.61 (0.01) | 249 (27) | 0.09 | 0.20 | 2.04 | 1.03 |
| R | 13.2 (1.8) | 5.59 (0.02) | 139 (12) | 0.11 | 0.11 | 1.93 | 1.07 |
| S | 11.8 (0.9) | 5.59 (0.02) | 154 (11) | 0.12 | 0.17 | 1.74 | 1.08 |
| T | 11.4 (2.2) | 5.68 (0.01) | 131 (31) | 0.07 | 0.16 | 2.92 | 1.06 |
| U | 10.8 (0.3) | 5.63 (0.01) | 204 (17) | 0.09 | 0.15 | 0.46 | 1.08 |
| V | 9.9 (0.6) | 5.68 (0.02) | 153 (12) | 0.10 | 0.15 | 0.88 | 1.06 |
| W | 11.7 (0.4) | 5.65 (0.01) | 172 (9) | 0.13 | 0.13 | 1.00 | 1.07 |
| X | 10.7 (0.4) | 5.63 (0.02) | 174 (19) | 0.15 | 0.18 | 0.46 | 1.08 |
| Y | 11.2 (1.0) | 5.69 (0.02) | 190 (22) | 0.00 | 0.01 | 1.50 | 1.04 |

TABLE 4

In-Process physical characteristics [mean (sd)] of ibuprofen tablets compressed at 12.5 kN

| Batch Code | Hardness (SCU) | Thickness (mm) | Disint. (s) | Friability (%) 6 min | Friability (%) 12 min | Weight Var. (%) | Tablet Density (g/mL) |
|---|---|---|---|---|---|---|---|
| A | 25.7 (3.5) | 5.33 (0.06) | 214 (32) | 0.05 | 0.12 | 2.42 | 1.15 |
| B | 22.8 (1.9) | 5.37 (0.03) | 87 (20) | 0.09 | 0.11 | 1.34 | 1.15 |
| C | 24.5 (1.3) | 5.22 (0.02) | 164 (9) | 0.11 | 0.14 | 0.94 | 1.17 |
| D | 21.2 (2.8) | 5.24 (0.04) | 149 (10) | 0.05 | 0 14 | 1.29 | 1.16 |
| E | 23.1 (2.0) | 5.26 (0.03) | 229 (18) | 0.07 | 0.09 | 1.99 | 1.16 |
| F | 21.5 (3.9) | 5.27 (0.07) | 231 (33) | 0.07 | 0.09 | 3.94 | 1.15 |
| G | 24.3 (1.6) | 5.15 (0.02) | 275 (32) | 0.03 | 0.10 | 1.36 | 1.18 |
| H | 21.6 (1.8) | 5.29 (0.03) | 147 (11) | 0.05 | 0.12 | 2.20 | 1.15 |
| I | 21.6 (1.8) | 5.33 (0.01) | 125 (21) | 0.04 | 0.05 | 1.55 | 1.14 |
| J | 20.6 (4.8) | 5.21 (0.09) | 268 (31) | 0.04 | 0.06 | 3.72 | 1.14 |
| K | 23.8 (2.3) | 5.26 (0.07) | 217 (13) | 0.00 | 0.04 | 2.03 | 1.16 |
| L | 23.5 (1.5) | 5.26 (0.03) | 384 (52) | 0.07 | 0.22 | 0.45 | 1.17 |
| M | 20.6 (2.2) | 5.26 (0.03) | 319 (19) | 0.28 | 0.33 | 1.32 | 1.15 |
| N | 25.9 (1.9) | 5.25 (0.03) | 225 (15) | 0.14 | 0.17 | 1.48 | 1.16 |
| O | 24.3 (0.9) | 5.27 (0.01) | 158 (15) | 0.12 | 0.22 | 0.62 | 1.16 |
| P | 26.2 (1.8) | 5.25 (0.03) | 148 (17) | 0.11 | 0.11 | 1.12 | 1.17 |
| Q | 21.6 (2.2) | 5.16 (0.04) | 239 (18) | 0.09 | 0.12 | 2.20 | 1.16 |
| R | 27.0 (3.1) | 5.15 (0.06) | 315 (19) | 0.11 | 0.12 | 2.21 | 1.18 |
| S | 24.1 (2.0) | 5.17 (0.03) | 173 (13) | 0.13 | 0.23 | 1.81 | 1.18 |
| T | 24.8 (2.6) | 5.18 (0.08) | 194 (14) | 0.13 | 0.13 | 2 98 | 1.17 |
| U | 23.8 (0.7) | 5.23 (0.01) | 242 (13) | 0.04 | 0.07 | 0.47 | 1.18 |
| V | 22.4 (1.2) | 5.27 (0.02) | 169 (15) | 0.01 | 0.01 | 1.12 | 1.16 |
| W | 26.7 (1.2) | 5.26 (0.02) | 265 (19) | 0.10 | 0.10 | 1.00 | 1.17 |
| X | 23.4 (0.6) | 5.22 (0.01) | 202 (13) | 0.12 | 0.16 | 0.54 | 1.18 |
| Y | 26.7 (1.9) | 5.18 (0.03) | 291 (25) | 0.00 | 0.01 | 1.60 | 1.17 |

TABLE 5

In-process physical characteristics [mean (sd)] of ibuprofen tablets compressed at 20 kN

| Batch Code | Hardness (SCU) | Thickness (mm) | Disint. (s) | Friability (%) 6 min | Friability (%) 12 min | Weight Var. (%) | Tablet Density (g/mL) |
|---|---|---|---|---|---|---|---|
| A | 31.7 (1.6) | 5.24 (0.08) | 356 (46) | 0.09 | 0.14 | 2.58 | 1.17 |
| B | 24.5 (4.7) | 5.22 (0.07) | 187 (16) | 0.05 | 0.07 | 1.40 | 1.16 |
| C | 27.9 (1.5) | 5.15 (0.04) | 189 (7) | 0.16 | 0 25 | 0.85 | 1.19 |
| D | 23.7 (1.0) | 5.19 (0.04) | 149 (14) | 0.11 | 0.11 | 1.11 | 1.17 |
| E | 29.5 (2.0) | 5.15 (0.06) | 232 (21) | 0.19 | 0 15 | 1.90 | 1.19 |
| F | 27.5 (2.9) | 5.21 (0.12) | 339 (19) | 0.09 | 0.12 | 3.50 | 1.18 |
| G | 29.4 (1.2) | 5.08 (0.05) | 382 (15) | 0.11 | 0.19 | 1.50 | 1.20 |
| H | 26.6 (1.3) | 5.23 (0.08) | 162 (10) | 0.09 | 0.24 | 2.24 | 1.18 |
| I | 25.7 (0.9) | 5.25 (0.03) | 122 (16) | 0.00 | 0.02 | 1.32 | 1.17 |
| J | 28.8 (2.3) | 5.16 (0.09) | 377 (18) | 0.06 | 0.07 | 3.35 | 1.18 |
| K | 26.4 (1.6) | 5.22 (0.07) | 212 (12) | 0.00 | 0.00 | 1.90 | 1.17 |
| L | 28.2 (1.9) | 5.20 (0.02) | 384 (27) | 0.12 | 0.16 | 0.45 | 1.18 |
| M | 27.0 (1.6) | 5.17 (0.05) | 389 (24) | 0.07 | 0.12 | 1.27 | 1.18 |
| N | 30.1 (1.6) | 5.16 (0.04) | 263 (8) | 0.14 | 0.14 | 1.27 | 1.18 |
| O | 26.4 (1.6) | 5.23 (0.02) | 182 (14) | 0.14 | 0.14 | 0.68 | 1.17 |
| P | 28.6 (1.9) | 5.23 (0.05) | 175 (9) | 0.05 | 0.10 | 1.15 | 1.18 |
| Q | 26.0 (1.5) | 5.12 (0.05) | 271 (13) | 0.09 | 0.14 | 2.15 | 1.18 |
| R | 30.7 (1.9) | 5.12 (0.08) | 331 (11) | 0.11 | 0.18 | 1.73 | 1.19 |
| S | 26.2 (1.2) | 5.13 (0.09) | 173 (16) | 0.09 | 0.10 | 1.61 | 1.19 |
| T | 27.6 (2.0) | 5.16 (0.09) | 206 (9) | 0.00 | 0.01 | 2.80 | 1.18 |
| U | 27.6 (1.3) | 5.18 (0.03) | 239 (5) | 0.09 | 0.09 | 0.57 | 1.19 |
| V | 25.6 (1.3) | 5.22 (0.04) | 156 (9) | 0.04 | 0.04 | 0.87 | 1.17 |
| W | 31.7 (1.2) | 5.18 (0.02) | 326 (40) | 0.07 | 0.09 | 0.94 | 1.19 |
| X | 27.3 (2.0) | 5.15 (0.03) | 214 (11) | 0.21 | 0.21 | 0.59 | 1.19 |
| Y | 32.1 (2.0) | 5.13 (0.04) | 348 (34) | 0.00 | 0.00 | 1.41 | 1.19 |

Physical characteristics of the formulations were measured after two weeks, at 40° C., 75% relative humidity for the 5, 12.5 and 20 kN samples. The results are listed in Tables 6–11.

TABLE 6

Physical characteristics [mean (sd)] of ibuprofen tablets compressed at 5 kN after 2 weeks storage at 40° C./75% RH

| Batch Code | Weight of 10 Tablets (g) | Hardness (SCU) | Thickness (mm) | Disint. (s) | Friability (%) 6 min | Friability (%) 12 min |
|---|---|---|---|---|---|---|
| A | 4.171 | 7.7 (1.3) | 6.20 (0.01) | 20 (3) | 0.42 | 0.76 |
| B | 4.229 | 9.6 (0.4) | 6.10 (0.02) | 28 (5) | 0.40 | 0.75 |
| C | 4.100 | 9.1 (1.2) | 5.84 (0.01) | 33 (2) | 0.32 | 0.61 |
| D | 4.159 | 9.1 (1.3) | 5.92 (0.01) | 34 (8) | 0.41 | 0.79 |
| E | 4.179 | 8.3 (1.2) | 5.97 (0.01) | 38 (7) | 0.30 | 0.57 |
| F | 3.955 | 7.5 (2.0) | 5.90 (0.01) | 16 (2) | 0.51 | 0.90 |
| G | 4.021 | 7.0 (0.7) | 5.80 (0.02) | 28 (2) | 0.38 | 0.72 |
| H | 4.058 | 10.2 (1.6) | 5.75 (0.02) | 35 (3) | 0.34 | 0.60 |
| I | 4.055 | 8.5 (0.9) | 5.97 (0.02) | 28 (4) | 0.22 | 0.45 |
| J | 4.050 | 8.0 (2.8) | 5.96 (0.03) | 45 (17) | 0.26 | 0.48 |
| K | 4.011 | 6.9 (0.7) | 5.95 (0.01) | 30 (5) | 0.25 | 0.55 |
| L | 4.213 | 9.1 (0.9) | 5.95 (0.03) | 238 (48) | 0.45 | 0.86 |
| M | 4.263 | 8.2 (0.6) | 6.04 (0.01) | 65 (14) | 0.58 | 0.96 |
| N | 4.155 | 9.4 (0.9) | 6.03 (0.03) | 56 (5) | 0.41 | 0.75 |
| O | 4.187 | 9.2 (0.6) | 6.05 (0.03) | 33 (3) | 0.43 | 0.82 |
| P | 4.201 | 11.1 (0.7) | 5.96 (0.01) | 33 (5) | 0.52 | 0.81 |
| Q | 4.043 | 6.6 (0.7) | 5.94 (0.03) | 35 (4) | 0.54 | 0.95 |
| R | 4.133 | 9.4 (1.2) | 5.93 (0.01) | 33 (5) | 0.51 | 0.85 |
| S | 4.121 | 9.1 (1.3) | 5.91 (0.02) | 27 (3) | 0.45 | 0.87 |
| T | 4.067 | 8.9 (1.9) | 5.92 (0.08) | 42 (13) | 0.55 | 0.96 |
| U | 4.239 | 9.5 (0.6) | 5.92 (0.02) | 52 (5) | 0.45 | 0.75 |
| V | 4.225 | 8.9 (0.9) | 6.06 (0.01) | 24 (3) | 0.46 | 0.86 |
| W | 4.145 | 8.8 (0.7) | 5.94 (0.02) | 41 (7) | 0.30 | 0.62 |
| X | 4.271 | 9.5 (0.6) | 5.95 (0.03) | 43 (2) | 0.56 | 0.93 |
| Y | 4.175 | 8.5 (1.0) | 6.04 (0.02) | 44 (4) | 0.48 | 0.90 |

TABLE 7

Physical characteristics [mean (sd)] of ibuprofen tablets compressed at 12.5 kN after 2 weeks storage at 40° C./75% RH

| Batch Code | Weight of 10 Tablets (g) | Hardness (SCU) | Thickness (mm) | Disint. (s) | Friability (%) 6 min | Friability (%) 12 min |
|---|---|---|---|---|---|---|
| A | 4.183 | 20.9 (4.1) | 5.61 (0.05) | 190 (113) | 0.29 | 0.46 |
| B | 4.197 | 19.9 (1.9) | 5.67 (0.02) | 60 (9) | 0.27 | 0.46 |
| C | 4.103 | 21.8 (1.3) | 5.45 (0.02) | 126 (21) | 0.23 | 0.44 |
| D | 4.155 | 21.0 (2.3) | 5.50 (0.02) | 104 (24) | 0.32 | 0.52 |
| E | 4.133 | 20.0 (2.5) | 5.47 (0.03) | 285 (28) | 0.24 | 0.38 |
| F | 4.078 | 19.7 (5.4) | 5.51 (0.06) | 186 (157) | 0.30 | 0.46 |
| G | 4.015 | 19.6 (1.5) | 5.33 (0.02) | 325 (32) | 0.25 | 0.36 |
| H | 4.104 | 18.0 (2.5) | 5.53 (0.02) | 91 (23) | 0.27 | 0.44 |
| I | 4.135 | 19.4 (1.2) | 5.62 (0.03) | 59 (10) | 0.23 | 0.34 |
| J | 3.947 | 16.7 (2.6) | 5.43 (0.02) | 269 (117) | 0.15 | 0.25 |
| K | 4.052 | 18.8 (3.2) | 5.51 (0.06) | 100 (27) | 0.16 | 0.30 |
| L | 4.210 | 20.0 (0.9) | 5.50 (0.02) | 201 (19) | 0.36 | 0.69 |
| M | 4.197 | 20.3 (2.0) | 5.55 (0.02) | 154 (37) | 0.38 | 0.60 |
| N | 4.191 | 23.4 (1.3) | 5.54 (0.03) | 154 (41) | 0.36 | 0.55 |
| O | 4.234 | 21.6 (1.5) | 5.59 (0.02) | 89 (9) | 0.38 | 0.60 |
| P | 4.211 | 23.1 (1.3) | 5.51 (0.04) | 109 (12) | 0.26 | 0.42 |
| Q | 4.103 | 19.1 (2.8) | 5.43 (0.05) | 176 (52) | 0.40 | 0.65 |
| R | 4.173 | 25.6 (2.6) | 5.44 (0.05) | 220 (57) | 0.31 | 0.54 |
| S | 4.086 | 20.3 (1.9) | 5.42 (0.04) | 87 (11) | 0.35 | 0.60 |
| T | 4.090 | 22.2 (3.8) | 5.43 (0.07) | 110 (16) | 0.34 | 0.56 |
| U | 4.224 | 22.2 (0.9) | 5.48 (0.02) | 129 (7) | 0.28 | 0.47 |
| V | 4.200 | 21.6 (1.2) | 5.56 (0.02) | 89 (11) | 0.32 | 0.59 |
| W | 4.162 | 21.9 (1.2) | 5.51 (0.02) | 212 (18) | 0.24 | 0.45 |
| X | 4.241 | 19.6 (0.7) | 3.49 (0.02) | 102 (9) | 0.40 | 0.67 |
| Y | 4.126 | 28.1 (1.2) | 5.47 (0.02) | 184 (18) | 0.35 | 0.59 |

TABLE 8

Physical characteristics [mean (sd)] of ibuprofen tablets compressed at 20 kN after 2 weeks storage at 40° C./75% RH

| Batch Code | Weight of 10 Tablets (g) | Hardness (SCU) | Thickness (mm) | Disint. (s) | Friability (%) 6 min | Friability (%) 12 min |
|---|---|---|---|---|---|---|
| A | 4.058 | 26.0 (1.6) | 5.38 (0.04) | 348 (82) | 0.24 | 0.51 |
| B | 4.196 | 25.7 (1.0) | 5.52 (0.03) | 130 (38) | 0.23 | 0.58 |
| C | 4.100 | 26.6 (0.9) | 5.34 (0.04) | 307 (32) | 0.21 | 0.35 |
| D | 4.128 | 22.5 (1.9) | 5.42 (0.03) | 177 (23) | 0.22 | 0.40 |
| E | 4.098 | 27.9 (2.5) | 5.35 (0.06) | 505 (19) | 0.17 | 0.30 |
| F | 4.012 | 23.8 (5.7) | 5.36 (0.15) | 457 (60) | 0.27 | 0.39 |
| G | 4.029 | 28.3 (1.5) | 5.27 (0.05) | 538 (30) | 0.22 | 0.33 |
| H | 4.146 | 24.5 (2.0) | 5.42 (0.09) | 273 (20) | 0.19 | 0.33 |
| I | 4.146 | 24.1 (1.9) | 5.51 (0.04) | 167 (25) | 0.15 | 0.25 |
| J | 4.061 | 26.3 (3.5) | 5.35 (0.11) | 523 (70) | 0.17 | 0.26 |
| K | 4.100 | 24.3 (1.5) | 5.48 (0.07) | 227 (17) | 0.15 | 0.23 |
| L | 4.198 | 24.8 (1.8) | 5.40 (0.03) | 409 (27) | 0.31 | 0.58 |
| M | 4.157 | 25.0 (1.5) | 5.41 (0.05) | 338 (26) | 0.35 | 0.54 |
| N | 4.202 | 29.2 (1.5) | 5.44 (0.04) | 352 (18) | 0.31 | 0.50 |
| O | 4.211 | 25.3 (2.0) | 5.50 (0.03) | 214 (15) | 0.32 | 0.49 |
| P | 4.214 | 25.3 (1.6) | 5.47 (0.04) | 204 (12) | 0.19 | 0.34 |
| Q | 4.128 | 24.3 (2.2) | 5.38 (0.06) | 289 (35) | 0.34 | 0.53 |
| R | 4.140 | 26.4 (1.6) | 5.37 (0.05) | 378 (19) | 0.30 | 0.51 |
| S | 4.109 | 23.5 (1.5) | 5.36 (0.05) | 171 (12) | 0.31 | 0.49 |
| T | 4.166 | 25.6 (1.9) | 5.44 (0.06) | 242 (56) | 0.30 | 0.40 |
| U | 4.209 | 25.1 (1.5) | 5.41 (0.03) | 218 (9) | 0.28 | 0.46 |
| V | 4.162 | 25.0 (1.3) | 5.46 (0.04) | 158 (21) | 0.21 | 0.40 |
| W | 4.191 | 30.1 (1.2) | 5.43 (0.03) | 402 (4) | 0.20 | 0.35 |
| X | 4.212 | 23.4 (1.5) | 5.39 (0.04) | 182 (10) | 0.34 | 0.53 |
| Y | 4.174 | 20.5 (1.6) | 5.39 (0.07) | 383 (24) | 0.47 | 0.70 |

TABLE 9

Physical Characteristics [mean (sd)] of ibuprofen tablets compressed at 5 kN after 4 weeks storage at RT

| Batch Code | Weight of 10 Tablets (g) | Hardness (SCU) | Thickness (mm) | Disint. (s) | Friability (%) 6 min | Friability (%) 12 min |
|---|---|---|---|---|---|---|
| A | 4.085 | 11.8 (1.6) | 5.92 (0.02) | 92 (23) | 0.15 | 0.27 |
| B | 4.123 | 14.5 (0.9) | 5.76 (0.02) | 80 (10) | 0.13 | 0.23 |
| C | 4.045 | 14.6 (1.3) | 5.60 (0.01) | 102 (9) | 0.14 | 0.24 |
| D | 4.035 | 12.3 (1.0) | 5.65 (0.01) | 136 (28) | 0.10 | 0.23 |
| E | 4.086 | 12.9 (1.8) | 5.75 (0.02) | 174 (26) | 0.07 | 0.17 |
| F | 3.925 | 11.1 (3.2) | 5.66 (0.02) | 152 (24) | 0.20 | 0.34 |
| G | 3.974 | 12.0 (0.7) | 5.59 (0.02) | 127 (20) | 0.16 | 0.28 |
| H | 3.998 | 15.9 (3.8) | 5.51 (0.02) | 101 (15) | 0.12 | 0.24 |
| I | 4.051 | 14.6 (1.6) | 5.67 (0.02) | 101 (9) | 0.07 | 0.12 |
| J | 4.004 | 12.0 (2.2) | 5.71 (0.04) | 264 (100) | 0.06 | 0.10 |
| K | 4.001 | 12.1 (1.8) | 5.65 (0.02) | 267 (36) | 0.03 | 0.09 |
| L | 4.097 | 11.2 (0.6) | 5.72 (0.03) | 325 (135) | 0.04 | 0.09 |
| M | 4.103 | 11.5 (0.7) | 5.75 (0.03) | 379 (128) | 0.05 | 0.07 |
| N | 4.056 | 13.9 (1.5) | 5.73 (0.03) | 195 (56) | 0.06 | 0.10 |
| O | 4.066 | 12.3 (1.2) | 5.74 (0.02) | 189 (59) | 0.09 | 0.17 |
| P | 4.102 | 15.2 (1.3) | 5.70 (0.02) | 137 (11) | 0.15 | 0.20 |
| Q | 3.942 | 9.9 (1.5) | 5.65 (0.03) | 299 (44) | 0.15 | 2.29 |
| R | 3.970 | 13.4 (1.8) | 5.63 (0.03) | 148 (45) | 0.10 | 0.15 |
| S | 4.043 | 13.6 (1.6) | 5.63 (0.03) | 90 (25) | 0.15 | 0.25 |
| T | 3.945 | 11.5 (2.3) | 5.66 (0.07) | 131 (47) | 0.06 | 0.17 |
| U | 4.094 | 13.0 (0.7) | 5.68 (0.02) | 177 (18) | 0 05 | 0.13 |
| V | 4.061 | 11.5 (0.6) | 5.74 (0.02) | 90 (21) | 0.10 | 0.21 |
| W | 4.055 | 13.6 (1.0) | 5.68 (0.02) | 162 (49) | 0.02 | 0.09 |
| X | 4.097 | 12.4 (0.6) | 5.67 (0.01) | 235 (29) | 0.10 | 0.23 |
| Y | 3.997 | 12.0 (0.7) | 5.72 (0.02) | 197 (18) | 0.05 | 0.14 |

TABLE 10

Physical characteristics [mean (sd)] of ibuprofen tablets compressed at 12.5 kN after 4 weeks storage at RT

| Batch Code | Weight of 10 Tablets (g) | Hardness (SCU) | Thickness (mm) | Disint. (s) | Friability (%) 6 min | Friability (%) 12 min |
|---|---|---|---|---|---|---|
| A | 4.011 | 25.1 (1.8) | 5.37 (2.08) | 254 (40) | 0.15 | 0.22 |
| B | 4.118 | 28.1 (1.6) | 5.42 (0.04) | 167 (17) | 0.11 | 0.17 |
| C | 4.065 | 29.4 (1.3) | 5.26 (0.17) | 264 (27) | 0.09 | 0.12 |
| D | 4.050 | 26.7 (2.6) | 5.29 (0.02) | 207 (26) | 0.07 | 0.15 |
| E | 4.079 | 29.1 (2.9) | 5.30 (0.02) | 468 (92) | 0.12 | 0.18 |
| F | 3.929 | 22.8 (5.6) | 5.26 (0.07) | 362 (120) | 0.11 | 0.17 |
| G | 3.979 | 27.0 (1.9) | 5.17 (0.02) | 435 (14) | 0.09 | 0.16 |
| H | 4.097 | 27.2 (3.4) | 5.34 (0.04) | 185 (32) | 0.11 | 0.20 |
| I | 4.100 | 28.2 (2.6) | 5.39 (0.04) | 152 (30) | 0.04 | 0.07 |
| J | 3.982 | 26.9 (5.0) | 5.25 (0.06) | 366 (46) | 0.06 | 0.09 |
| K | 3.982 | 26.6 (2.3) | 5.24 (0.03) | 252 (26) | 0.06 | 0.07 |
| L | 4.069 | 27.3 (1.2) | 5.29 (0.02) | 428 (13) | 0.07 | 0.10 |
| M | 4.053 | 27.3 (2.0) | 5.31 (0.02) | 369 (31) | 0.06 | 0.09 |
| N | 4.024 | 30.2 (2.9) | 5.26 (0.03) | 272 (35) | 0.07 | 0.11 |
| O | 4.068 | 29.1 (1.6) | 5.31 (0.02) | 180 (11) | 0.07 | 0.10 |
| P | 4.053 | 29.5 (1.8) | 5.27 (0.03) | 274 (15) | 0.15 | 0.23 |
| Q | 4.022 | 28.5 (3.4) | 5.22 (0.05) | 447 (51) | 0.14 | 0.16 |
| R | 4.006 | 32.7 (4.2) | 5.18 (0.05) | 505 (36) | 0.09 | 0.15 |
| S | 3.964 | 27.5 (2.8) | 5.20 (0.02) | 226 (36) | 0.13 | 0.21 |
| T | 3.944 | 27.5 (3.2) | 5.19 (0.05) | 264 (18) | 0.10 | 0.15 |
| U | 4.082 | 28.5 (1.0) | 5.27 (0.02) | 251 (11) | 0.10 | 0.18 |
| V | 4.051 | 27.0 (1.3) | 5.30 (0.03) | 225 (10) | 0.09 | 0.15 |
| W | 4.090 | 30.5 (2.0) | 5.28 (0.02) | 571 (20) | 0.07 | 0.11 |
| X | 4.070 | 27.2 (0.4) | 5.25 (0.01) | 236 (11) | 0.06 | 0.14 |
| Y | 3.975 | 28.5 (3.7) | 5.21 (0.03) | 461 (65) | 0.04 | 0.09 |

TABLE 11

Physical characteristics [mean (sd)] of Ibuprofen tablets compressed at 20 kN after 4 weeks storage at RT

| Batch Code | Weight of 10 Tablets (g) | Hardness (SCU) | Thickness (mm) | Disint. (s) | Friability (%) 6 min | 12 min |
|---|---|---|---|---|---|---|
| A | 3.988 | 33.2 (2.6) | 5.19 (0.06) | 550 (40) | 0.12 | 0.19 |
| B | 4.031 | 30.4 (4.2) | 5.25 (0.07) | 274 (25) | 0.10 | 0.16 |
| C | 4.032 | 31.6 (1.3) | 5.19 (0.02) | 338 (11) | 0.10 | 0.16 |
| D | 4.044 | 23.3 (1.6) | 5.23 (0.05) | 201 (30) | 0.09 | 0.15 |
| E | 4.027 | 35.8 (0.9) | 5.21 (0.05) | 608 (20) | 0.12 | 0.19 |
| F | 4.042 | 31.6 (2.5) | 5.18 (0.05) | 507 (59) | 0.12 | 0.19 |
| G | 4.003 | 33.9 (1.5) | 5.12 (0.04) | 621 (23) | 0.14 | 0.19 |
| H | 4.018 | 30.1 (1.5) | 5.19 (0.06) | 312 (21) | 0.14 | 0.21 |
| I | 4.112 | 30.8 (1.9) | 5.32 (0.04) | 260 (14) | 0.02 | 0.06 |
| J | 4.020 | 34.5 (1.9) | 5.20 (0.07) | 475 (28) | 0.06 | 0.10 |
| K | 4.056 | 32.6 (1.8) | 5.24 (0.07) | 328 (27) | 0.05 | 0.07 |
| L | 4.072 | 33.5 (1.6) | 5.21 (0.03) | 417 (22) | 0.06 | 0.11 |
| M | 4.044 | 33.2 (2.5) | 5.21 (0.05) | 481 (9) | 0.06 | 0.09 |
| N | 4.061 | 36.4 (0.9) | 5.21 (0.07) | 352 (12) | 0.09 | 0.12 |
| O | 4.060 | 31.4 (2.0) | 5.25 (0.03) | 258 (8) | 0.07 | 0.10 |
| P | 4.094 | 32.1 (1.9) | 5.24 (0.04) | 347 (8) | 0.13 | 0.21 |
| Q | 3.985 | 30.7 (2.2) | 5.14 (0.07) | 511 (13) | 0.10 | 0.11 |
| R | 4.081 | 37.3 (2.2) | 5.20 (0.06) | 456 (23) | 0.06 | 0.14 |
| S | 3.995 | 29.9 (0.9) | 5.17 (0.05) | 298 (10) | 0.09 | 0.14 |
| T | 4.060 | 33.2 (1.5) | 5.19 (0.06) | 328 (23) | 0.04 | 0.11 |
| U | 4.076 | 32.6 (0.7) | 5.20 (0.02) | 318 (11) | 0.09 | 0.15 |
| V | 4.066 | 28.9 (2.9) | 5.25 (0.04) | 268 (12) | 0.07 | 0.16 |
| W | 4.090 | 37.0 (1.5) | 5.21 (0.03) | 662 (29) | 0.06 | 0.13 |
| X | 4.068 | 31.3 (1.3) | 5.19 (0.04) | 343 (17) | 0.10 | 0.21 |
| Y | 4.046 | 37.0 (2.2) | 5.17 (0.05) | 665 (26) | 0.05 | 0.11 |

The data in Tables 3–11 show that tablets of the present invention may be compressed across a wide area of compression forces with no substantial change in the disintegration time of the tablet. The data also indicate that the tablets have good compression performance since they can be compressed over a wide range of compression forces and are relatively insensitive to press speed. In fact, it has also been established that embodiments of the present invention are stable up to about 12 month(s) at 25° C., 60% relative humidity. That is, there is no substantial change in dissolution characteristics or no substantial change in disintegration time after 12 months.

EXAMPLE 2

Ibuprofen/hydrocodone tablets were prepared with the amount of the following ingredients as follows:

(a) 50% ibuprofen;
(b) 1.88% hydrocodone bitartrate;
(c) 1.5% colloidal silicon dioxide;
(d) 19.3% microcrystalline cellulose;
(e) 8% sodium croscarmellose;
(f) 3.25% hydroxypropyl methylcellulose;
(g) 15.6% corn starch; and
(h) 0.5% magnesium stearate.

Hydrocodone bitartrate was passed through a #20 mesh handscreen. Ibuprofen (50%), and colloidal silicon dioxide (0.75%) were passed through a Frewitt SG Turbo Sieve equipped with a 1.0 mm round-hole screen, an angle bar, a cloth skirt, and a polyethylene-line collecting drum at speed setting 5 (approximately 1030 rpm). Microcrystalline Cellulose (9.5%), croscarmellose sodium (4.0%), corn starch (10.6%) and hydroxypropyl methylcellulose (3.3%) were passed through the Turbosieve at the same settings. The screened powders were introduced into a Lodige MGT-600 mixer and mixed for 5 minutes with plow speed at approximately 103 rpm and NO choppers. Water was added to the mixer over a 10 minute period using a stainless steel transfer container with a valve while mixing with plows at about 103 rpm and choppers at slow speed. The wet material was mixed for another 15 minutes until a Wattmeter of 15–16 kw was reached.

To dry the material a Glatt fluid-bed dryer was preheated by running it for 2.5 minutes at 60° C. inlet air temperature at 3500 m³/hr. The exhaust blower bypass speed was set at about 40%, the filter shaking interval for about 2 minutes and the filter shaking duration was for 5 seconds. The material was placed in the dryer for drying. The inlet air was decreased to 2500 m³/hr and the inlet air temperature to 55° C. after thirty minutes. The material was dried until an LOD of less than 0.5% was reached.

The dried granulation was passed through a Fitzmill using a #20 mesh wire screen 1536–0200 with knives forward at medium speed. The remaining microcrystalline cellulose and the colloidal silicon dioxide was passed, alternatively, through a Frewitt SG Turbo Sieve equipped with a 1.0 mm round-hole screen, an angle bar, a cloth skirt, and a polyethylene-lined collecting drum. The speed setting was set at approximately 1030 rpm.

The milled granulation, the remaining croscarmellose, the screened colloidal silicon dioxide, the microcrystalline cellulose, and the corn starch were introduced into a Littleford FKM-3000 mixer through a chute and mixed for 3 minutes at fast speed. Magnesium stearate was passed through a Frewitt Turbo Sieve equipped with a 1.0 mm round hold screen, an angle bar, a cloth skirt and a polyethylene line collecting drum. The speed setting was at about 1030 rpm. The magnesium stearate was then added to the mixture and mixed for 3 minutes at fast speed. The final blend was discharged through a cloth sleeve into tared totes with inserts with minimum jogging.

The composition was compressed into tablets using a Kilian TX-32 tablet press and 13/32" round tooling with "VP". Tablets made according to this method showed no picking or sticking. These tablets were filmed coated.

Dissolution testing was performed on the tablets in 900 ml of pH 7.4 phosphate buffer, at 37° C. using baskets at 150 rpm. The results showed that 100% of the ibuprofen and the hydrocodone was released in about 10 minutes.

These tablets were stable up to about 12 month(s) at 25° C., 60% relative humidity. There was also no substantial change in dissolution characteristics or no substantial change in disintegration time up to and after 12 months. The tablets were also stable for up to 6 months at 40° C., 75% relative humidity with no significant changes in dissolution characteristics or disintegration time.

EXAMPLE 3

Figure 2:
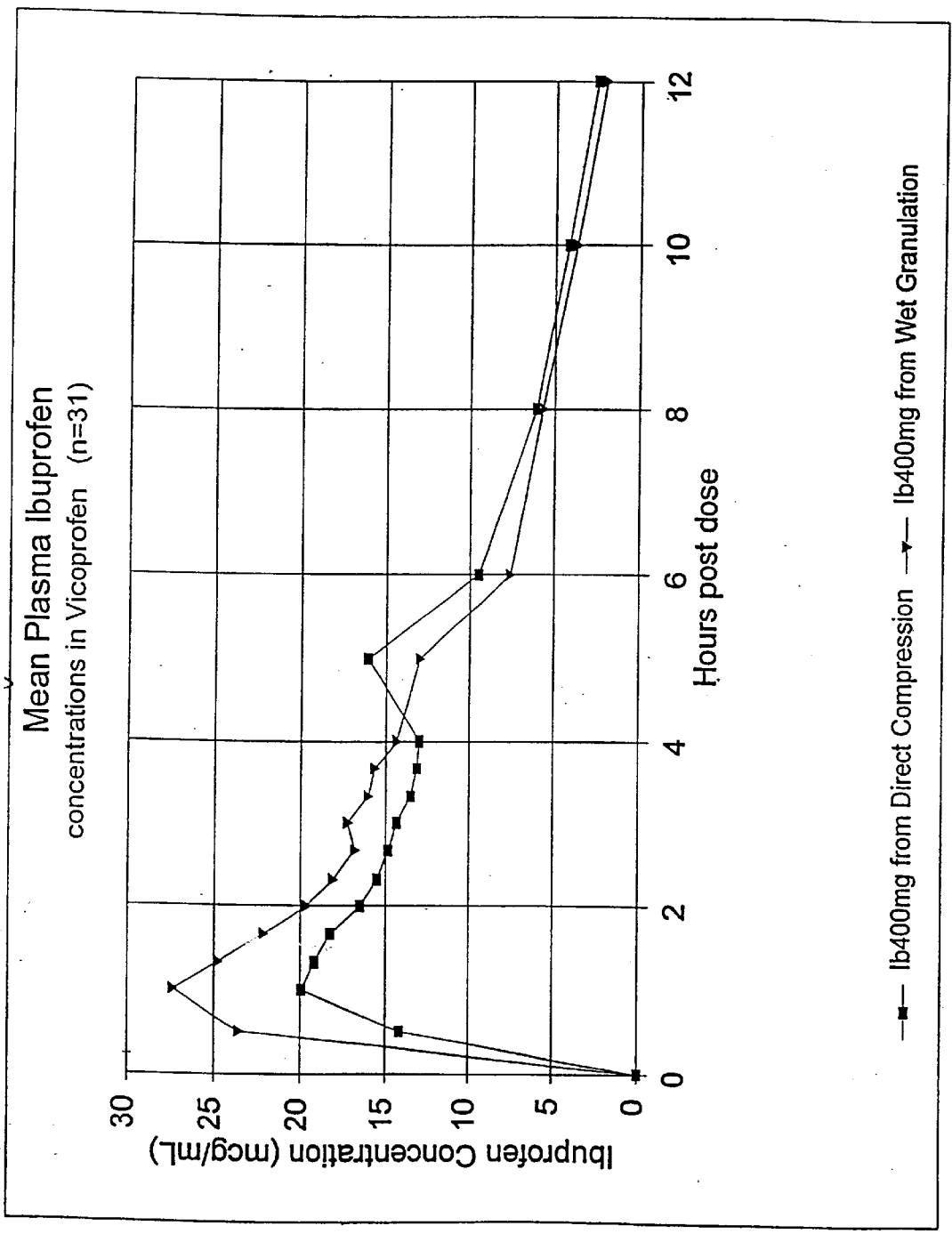
FIG. 2 is a graph of the plasma concentration of ibuprofen over time provided by an embodiment of the present invention.

An open-label, single-dose, randomized, two-way crossover bioequivalence study was performed in normal, healthy adult subjects. Treatments administered to each subject were two direct compression 200/7.5 (ibuprofen/hydrocodone bitartrate) tablets and two wet compression tablets of the same strength and active ingredient prepared according to Example 2. Thirty-three subjects received the direct compression tablets and thirty-one subjects received the wet granulation tablets. Blood sampling was done immediately before and 30 and 60 minutes, one hour and twenty minutes, one hour and forty minutes, two hours, two hours and twenty minutes, two hours and forty minutes, three hours, three hours and twenty minutes, three hours and forty minutes and four, five, six, eight, ten and twelve hours after each dose. The plasma ibuprofen and hydrocodone levels were measured at each interval. Analysis of variance model was used to analyze the data. The analysis indicated that the direct compression formulation and the formulation prepared according to the present invention indicates were bioequivalent. The results are graphed in FIGS. 1 & 2.

The invention has been described with reference to various specific embodiments. However, many variations and modifications may be made while remaining within the scope and spirit of the invention.

We claim:

1. A pharmaceutical tablet composition comprising ibuprofen and hydrocodone bitartrate, said tablet having been prepared by a method comprising the steps of:
   (a) granulating ibuprofen, hydrocodone bitartrate, colloidal silicon dioxide, a disintegrant, a filler, and starch to form granules, wherein said granulating step comprises a wet granulation process;
   (b) blending the granules with extra-granular material comprised of a lubricant and at least one excipient to form a blend of granules and extra granular material wherein the composition is substantially free of lactose and polyvinylpyrrolidone and wherein the blend flows well, has good compression performance, and can be compressed over a wide range of compression forces with no substantial change in the disintegration time of a tablet made from such blend; and
   (c) compressing the blend into a tablet, wherein said ibuprofen, said hydrocodone bitartrate and said lubricant are present in said tablet in a single phase.

2. The pharmaceutical tablet composition as recited in claim 1, wherein the ibuprofen is provided in a range of about 25% to about 63%, by total weight of the tablet; the hydrocodone bitartrate is provided in a range of about 0.6% to about 3.8%, by total weight of the tablet; the colloidal silicon dioxide is provided in a range of about 0.5% to about 3% by total weight of the tablet; the filler is selected from the group consisting of microcrystalline cellulose and powdered cellulose and is provided in range of the total weight of the tablet of about 10% to about 42%; the disintegrant is selected from the group consisting of croscarmellose sodium, crospovidone, and sodium starch glycolate and is provided in a range, of the total weight of the tablet, of about 4% to about 10%; the starch is provided in a range, of the total weight of the tablet composition, of about 11% to about 20%; and the lubricant is provided in an amount less than 1% by weight of the total weight of the tablet; and wherein a binder is provided in a range, of the total weight of the tablet composition, of about 2% to less than 6%, and the binder comprises an alkylhydroxy methylcellulose;

and wherein the granule comprises granulate material comprised of:
   1) the ibuprofen,
   2) the hydrocodone,
   3) about 0.5% to about 2.0%, of the total weight of the tablet composition, of colloidal silicon dioxide,
   4) about 9.5% up to about 22%, of the total weight of the tablet composition, of filler,
   5) about 4%, of the total weight of the tablet composition, of disintegrant, and
   6) about 6% to about 12%, of the total weight of the tablet composition of starch;
wherein the extra granule material comprises the remaining amount of the tablet material; the composition provided in the substantial absence of lactose and/or polyvinylpyrrolidone and wherein the composition flows well, has good compression performance, and can be compressed over a wide range of compression forces with no substantial change in the disintegration time of the tablet.

3. The pharmaceutical tablet composition as recited in claim 2, wherein the weight of the filler is provided in range, of the total weight of the tablet composition, of about 15% to about 25%.

4. The pharmaceutical tablet composition as recited in claim 2, wherein the weight of the disintegrant is provided in a range of about 6% to about 8%.

5. The pharmaceutical tablet composition as recited in claim 3, wherein the weight of the disintegrant is provided in a range of about 6% to about 8%.

6. The pharmaceutical tablet composition as recited in claim 2, wherein the weight of the colloidal silicon dioxide is in a range of the total weight of the tablet, of about 1.5% to about 2%.

7. The pharmaceutical tablet composition as recited in claim 3, wherein the weight of the colloidal silicon dioxide is in a range of the total weight of the tablet, of about 1.5% to about 2%.

8. The pharmaceutical tablet composition as recited in claim 4, wherein the weight of the colloidal silicon dioxide is in a range of the total weight of the tablet, of about 1.5% to about 2%.

9. The pharmaceutical tablet composition as recited in claim 5, wherein the weight of the colloidal silicon dioxide is in a range of the total weight of the tablet, of about 1.5% to about 2%.

10. The pharmaceutical tablet composition as recited in claim 2, wherein the weight of the binder is in a range, of the total weight of the tablet, of about 3% to about 4%.

11. The pharmaceutical tablet composition as recited in claim 3, wherein the weight of the binder is in a range, of the total weight of the tablet, of about 3% to about 4%.

12. The pharmaceutical tablet composition as recited in claim 4, wherein the weight of the binder is in a range, of the total weight of the tablet, of about 3% to about 4%.

13. The pharmaceutical tablet composition as recited in claim 5, wherein the weight of the binder is in a range, of the total weight of the tablet, of about 3% to about 4%.

14. The pharmaceutical tablet composition as recited in claim 6, wherein the weight of the binder is in a range, of the total weight of the tablet, of about 3% to about 4%.

15. The pharmaceutical tablet composition as recited in claim 7, wherein the weight of the binder is in a range, of the total weight of the tablet, of about 3% to about 4%.

16. The pharmaceutical tablet composition as recited in claim 8, wherein the weight of the binder is in a range, of the total weight of the tablet, of about 3% to about 4%.

17. The pharmaceutical tablet composition as recited in claim 9, wherein the weight of the binder is in a range, of the total weight of the tablet, of about 3% to about 4%.

18. The pharmaceutical tablet composition as recited in claim 2, wherein the weight of the starch is in a range, of the total weight of the tablet, of about 6% to about 8%.

19. The pharmaceutical tablet composition as recited in claim 3, wherein the weight of the starch is in a range, of the total weight of the tablet, of about 6% to about 8%.

20. The pharmaceutical tablet composition as recited in claim 4, wherein the weight of the starch is in a range, of the total weight of the tablet, of about 6% to about 8%.

21. The pharmaceutical tablet composition as recited in claim 5, wherein the weight of the starch is in a range, of the total weight of the tablet, of about 6% to about 8%.

22. The pharmaceutical tablet composition as recited in claim 6, wherein the weight of the starch is in a range, of the total weight of the tablet, of about 6% to about 8%.

23. The pharmaceutical tablet composition as recited in claim 7, wherein the weight of the starch is in a range, of the total weight of the tablet, of about 6% to about 8%.

24. The pharmaceutical tablet composition as recited in claim 8, wherein the weight of the starch is in a range, of the total weight of the tablet, of about 6% to about 8%.

25. The pharmaceutical tablet composition as recited in claim 9, wherein the weight of the starch is in a range, of the total weight of the tablet, of about 6% to about 8%.

26. The pharmaceutical tablet composition as recited in claim 10, wherein the weight of the starch is in a range, of the total weight of the tablet, of about 6% to about 8%.

27. The pharmaceutical tablet composition as recited in claim 11, wherein the weight of the starch is in a range, of the total weight of the tablet, of about 6% to about 8%.

28. The pharmaceutical tablet composition as recited in claim 12, wherein the weight of the starch is in a range, of the total weight of the tablet, of about 6% to about 8%.

29. The pharmaceutical tablet composition as recited in claim 13, wherein the weight of the starch is in a range, of the total weight of the tablet, of about 6% to about 8%.

30. The pharmaceutical tablet composition as recited in claim 14, wherein the weight of the starch is in a range, of the total weight of the tablet, of about 6% to about 8%.

31. The pharmaceutical tablet composition as recited in claim 15, wherein the weight of the starch is in a range, of the total weight of the tablet, of about 6% to about 8%.

32. The pharmaceutical tablet composition as recited in claim 16, wherein the weight of the starch is in a range, of the total weight of the tablet, of about 6% to about 8%.

33. The pharmaceutical tablet composition as claimed in claim 17, wherein the weight of the starch is in a range, of the total weight of the tablet, of about 6% to about 8%.

34. A pharmaceutical tablet composition comprising ibuprofen and hydrocodone bitartrate, said tablet having been prepared by a method comprising the steps of:
    (a) granulating ibuprofen, hydrocodone bitartrate, colloidal silicon dioxide, a disintegrant, a filler and starch to form granules, wherein said granulating step comprises a wet granulation process;
    (b) blending the granules with extra-granular material to form a blend of granules and extra granular material wherein the composition is substantially free of lactose and polyvinylpyrrolidone and wherein the blend flows well, has good compression performance, and can be compressed over a wide range of compression forces with no substantial change in the disintegration time of a tablet made from such blend; and
    (c) compressing the blend into a tablet, wherein said granules and said extragranular material are present in said tablet in a single phase.

35. A pharmaceutical tablet composition comprising ibuprofen and hydrocodone bitartrate, said tablet having been prepared by a method comprising the steps of:
    (a) granulating ibuprofen, hydrocodone bitartrate, colloidal silicon dioxide, a disintegrant, a filler and starch to form granules, wherein said granulating step comprises a wet granulation process;
    (b) blending the granules with extra-granular material comprised of a lubricant and at least one excipient to form a blend of granules and extra granular material wherein the composition is substantially free of lactose and polyvinylpyrrolidone and wherein the blend flows well and has good compression performance; and
    (c) compressing the blend into a tablet, wherein said ibuprofen, said hydrocodone bitartrate and said lubricant are present in said tablet in a single phase.

36. A pharmaceutical tablet composition comprising ibuprofen and hydrocodone bitartrate, said tablet having been prepared by a method comprising the steps of:
    (a) granulating by means of a wet granulation process ibuprofen, hydrocodone, a filler and starch to form granules;
    (b) blending the granules with extra-granular material to form a blend of granules and extra granular material wherein the composition is substantially free of lactose and polyvinylpyrrolidone and wherein the blend flows well, and has good compression performance; and
    (c) compressing the blend into a tablet, wherein said granules and said extragranular material are present in said tablet in a single phase.

* * * * *